(12) United States Patent
Abolfathi et al.

(10) Patent No.: US 7,904,307 B2
(45) Date of Patent: Mar. 8, 2011

(54) HEALTH-CARE E-COMMERCE SYSTEMS AND METHODS

(75) Inventors: Amir Abolfathi, Woodside, CA (US); Ike Udechuku, San Francisco, CA (US); Phillips Alexander Benton, Mountain View, CA (US); Beth Ann Cooney, Sunnyvale, CA (US); Keith Wolf, San Francisco, CA (US)

(73) Assignee: Align Technology, Inc., San Jose, CA (US)

( * ) Notice: Subject to any disclaimer, the term of this patent is extended or adjusted under 35 U.S.C. 154(b) by 866 days.

(21) Appl. No.: 11/271,360

(22) Filed: Nov. 10, 2005

(65) Prior Publication Data

US 2006/0064329 A1   Mar. 23, 2006

Related U.S. Application Data

(63) Continuation of application No. 09/534,461, filed on Mar. 24, 2000, now abandoned.

(51) Int. Cl.
*G06Q 50/00* (2006.01)
*G06F 19/00* (2006.01)

(52) U.S. Cl. .................................. 705/2; 705/3; 600/300
(58) Field of Classification Search .................. 705/2, 3; 600/300; 433/68, 24, 213
See application file for complete search history.

(56) References Cited

U.S. PATENT DOCUMENTS

| | | | | | |
|---|---|---|---|---|---|
| 5,027,281 | A | * | 6/1991 | Rekow et al. | 700/182 |
| 5,131,843 | A | * | 7/1992 | Hilgers et al. | 433/20 |
| 5,683,243 | A | * | 11/1997 | Andreiko et al. | 433/3 |
| 6,283,761 | B1 | * | 9/2001 | Joao | 434/236 |
| 6,540,512 | B1 | * | 4/2003 | Sachdeva et al. | 433/24 |

* cited by examiner

*Primary Examiner* — Robert W Morgan
(74) *Attorney, Agent, or Firm* — Townsend and Townsend and Crew LLP

(57) ABSTRACT

A virtual health-care electronic commerce community includes a network to communicate information relating to the community; one or more patients coupled to the network; one or more treating professionals coupled to the network; and a server coupled to the network, the server storing data for each patient and performing patient data visualization in response to a user request.

11 Claims, 14 Drawing Sheets

HEALTH-CARE E-COMMERCE SYSTEMS AND METHODS

CROSS-REFERENCES TO RELATED APPLICATIONS

The present application is a continuation of U.S. patent application Ser. No. 09/534,461, filed Mar. 24, 2000, the full disclosure of which is incorporated herein by reference.

BACKGROUND OF THE INVENTION

The Internet has become a significant medium for communication and commerce and has enabled millions of people to share information and conduct business electronically. The unique characteristics of the Internet such as its ability to provide enhanced communication, rich text, and graphic environment provide an ideal support for a wide variety of electronic commerce transactions. For example, a consumer can search, review, and extensively shop a number of competing chains in an instant. As such, consumers benefit by being able to obtain a good price relatively quickly and easily.

On-line retailers also benefit, since these retailers can carry a larger number of products at a lower cost and with greater merchandising flexibility without the physical constraints faced by traditional retailers. Additionally, they can assist the consumer's purchase decision by providing relevant information and enabling consumers to shop at their convenience by remaining open 24 hours a day, seven days a week. Online retailers can also provide personalized services and use direct marketing efforts based on information provided by customers.

As such, the Internet has evolved into a unique sales and marketing channel. The ubiquity and convenience of the Internet makes it ideal for dispensing information on certain topics that traditionally require visits to specialists. For example, certain consumers may be interested in products and services associated with orthodontics and dentofacial orthopedics that specializes in the diagnosis, prevention and treatment of dental and facial irregularities ("malocclusion" or "bad bite"). The orthodontic treatment process typically uses corrective appliances such as braces and/or other fixed or removable appliances to bring the teeth, lips and jaws into proper alignment and to achieve a facial balance. The pervasiveness of the Internet makes it an ideal source for information relating to these products and services.

BRIEF SUMMARY OF THE INVENTION

In one aspect, a virtual health-care electronic commerce community includes a network to communicate information relating to the community; one or more patients coupled to the network; one or more treating professionals coupled to the network; and a server coupled to the network, the server storing data for each patient and performing patient data visualization in response to a user request.

Implementations of the above aspect may include one or more of the following. The treating professional can view one or more of the following patient data visualization over the network: a right buccal view; a left buccal view; a posterior view; an anterior view; a mandibular occlusal view; a maxillary occlusal view; an overjet view; a left distal molar view; a left lingual view; a lingual incisor view; a right lingual view; a right distal molar view; an upper jaw view; and a lower jaw view. The treating professionals can include dentists or orthodontists. One or more partners can be connected to the network. The partners can be a financing partner, a supplier, or a delivery company. The treating professionals can perform office management operations using the server. The office management operations include one or more of the following: patient scheduling, patient accounting, and claim processing. The patients and the treating professionals can access the server using browsers.

In another aspect, a method for performing dental-related electronic commerce includes transmitting teeth data associated a patient from a dental server to a treating professional computer over the Internet upon an authorized request; displaying a three-dimensional computer model of the teeth at the treating professional computer using a browser; allowing a treating professional to manipulate the three-dimensional computer model of the teeth using the browser; transmitting the computer model from the treating professional computer to the server; and generating an appliance to treat the patient based on the computer model of the teeth.

Implementations of the above aspect may include one or more of the following. The system can provide financing options for the patient using one or more financing partners. The system can offer an on-line shop geared to the patient's dental requirements. The system also allows a treating professional to manipulate the three-dimensional computer model of the teeth using the browser further comprises displaying a plurality of dental views.

A treating professional can manipulate the three-dimensional computer model of the teeth using the browser further comprises clicking on a tooth to adjust its position. The system can display x, y and z axis to allow the treating professional to adjust the position of the tooth. Supplemental services can also be offered to the patient, including teeth whitening services.

In another aspect, a server supports a health-care electronic commerce community with one or more patients and one or more service providers. The server includes a processor adapted to communicate with a network; a data storage device coupled to the processor and adapted to store data for each patient; and software to communicate 3D patient data in response to a client request.

Implementations can include one or more of the following. A browser can receive the client request and transmitting the request to the server. The browser can use a viewer plug-in to visualize patient data in 3D. The providers can provide health-care service such as dentistry applications, cosmetic augmentation, hair-care enhancements, liposuction, plastic or reconstructive surgery.

Advantages of the system may include one or more of the following. The system supports a virtual community of dental patients, dentists, specialists such as orthodontists and oral surgeons, financial institutions, benefit providers and the providers of dental equipment or services. For treating professionals, such as dentists and orthodontists, the system provides a one-stop solution for planning patient treatments, managing communication with patients, storing patient records and sharing records with relevant persons outside the doctor's office. The system can act as the repository for the file notes and visual imagery (photographs, x-rays and virtual treatment plans) associated with the course of treatment. The doctors will control access to the centralized patient file. Various tools are provided to support the interpretation of information and the diagnostic process. For example, the system allows the doctors to retrieve, and analyze patient information and to simulate using two and three-dimensional visual imagery of the patient's teeth and other anatomical structures. The system supports visualization of the expected outcome of a particular course of treatment. Working together with the patient these images can enhance the patient's understanding of the benefits of treatment and act as a valuable selling tool for the doctor. The system also provides diagnostic decision-support capabilities such as visualizing the placement of implantations, veneers and crowns before or after a course of treatment to straighten the teeth. The system provides an animated prediction of the suggested treatment that helps the patient and the doctor to visualize the pace of treatment. Using these tools, the doctor can easily and quickly view and/or edit the treatment plan. When doctor and patient choose the final treatment plan the system disseminates aspects of the plan and the relevant patient records to the appropriate members of the virtual community, thus reducing the cost and delay associated with tradition physical shipment of patient information. Aspects of the final treatment plan can be used to generate appliances used in the physical treatment. The information associated with the patient's treatment (visual images, virtual treatment plans, file notes and the like) are digitized and maintained in a central storage facility in a secure manner. Doctors and patients can have access to these files without the need to extract files and models from storage and with reduced risk of records being misplaced.

Administratively, the system allows the office to be managed more efficiently without requiring the treating professional to purchase and maintain special software. The system keeps track of all patients that need to be contacted for an appointment. Scheduling can be done automatically or can be customized to the office's preference and availability of treating professionals and supporting resources. Based on the appointments, the system can electronically mail (email) patients with reminders. Alternatively, the system can print reminder cards that can be mailed to patients reminding them of their appointment. The system can also automatically generate personalized correspondence to patients relating to data collected in the initial exam and treatment recommendations. Moreover, the patient can review the proposed treatment with the treating professional anywhere.

The system also simplifies and streamlines the processing of insurance claims to produce an orderly flow of information. Insurance claims can flow through the treating professional's office from pre-authorization to continuation of treatment with a minimal amount of intervention. The system also provides accounting functions to check out patients, post charges, setup contracts, add comments to ledgers, post payments, adjust ledgers, and display all transactions applied to specific ledgers.

Moreover, the treating professionals can leverage the collective purchasing power of the system by ordering being able to order supplies required by patients directly through the system at a discount. These supplies can be directly shipped to the patients, thus avoiding overhead costs associated with handling the supplies. Further, information reviewed or generated by the treating professionals is provided through a secure on-line connection. Thus, the patient's privacy as well as the treating professional's sensitive office information is not compromised.

For patients, the system provides a broad array of dental-care resources that help consumers find answers to their critical dental questions and make informed purchasing decisions. The system also enables people to share their experiences and to support one another in managing their medical conditions. This is done through forums where Internet users with interests and concerns about their dental health can interact with each other, to interact in a community environment and to access content created by others.

The system is convenient to use and provides informative shopping experience through which dental care services and dental-related products can be dispensed. Consumers can access the system using an intuitive, easy-to-use shopping interface that is available 24 hours a day, seven days a week. Consumers can shop quickly and conveniently from anywhere Internet access is available. For example, a customer can store his or her dental history and other relevant dental information, as well as create personalized shopping lists for quick and easy reordering of his or her dental supplies.

BRIEF DESCRIPTION OF THE DRAWINGS

FIG. 11 is an exemplary home page of the web-based interface of the present invention.

Figure 12:
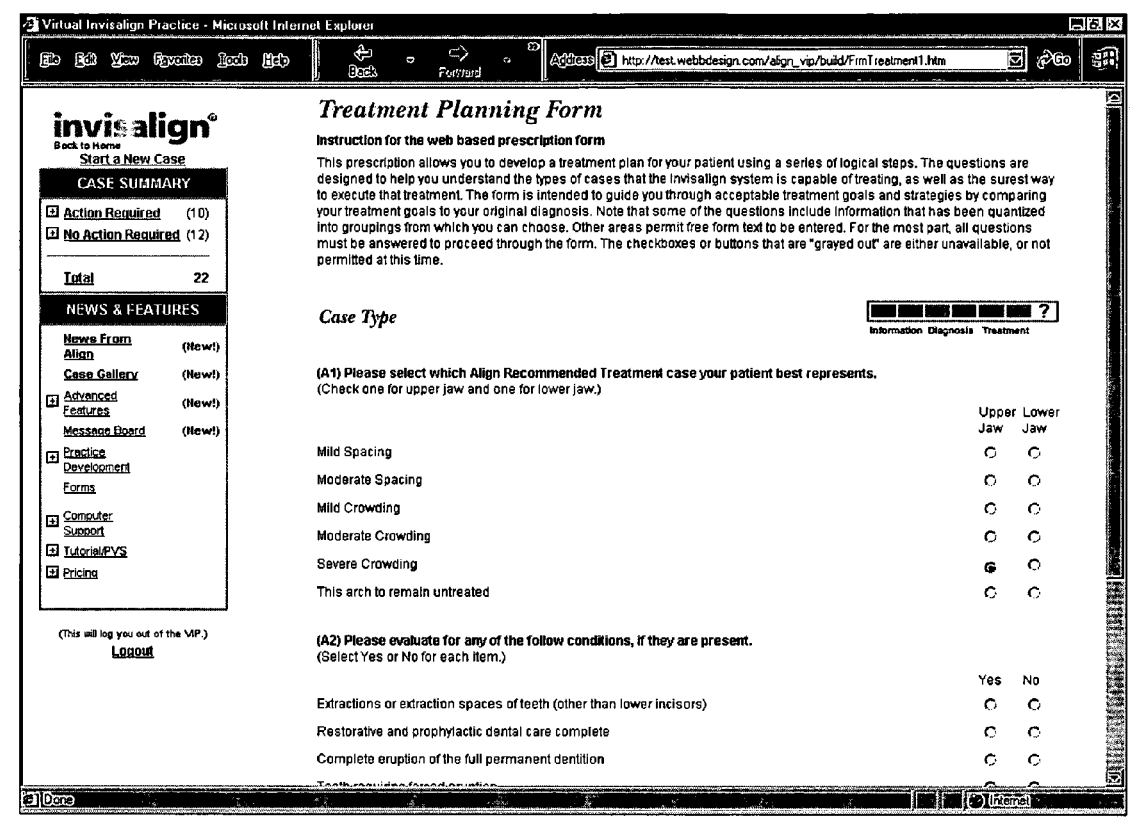

FIG. 12 is a Treatment Preference template according to the present invention.

DETAILED DESCRIPTION OF THE INVENTION

Figure 1:
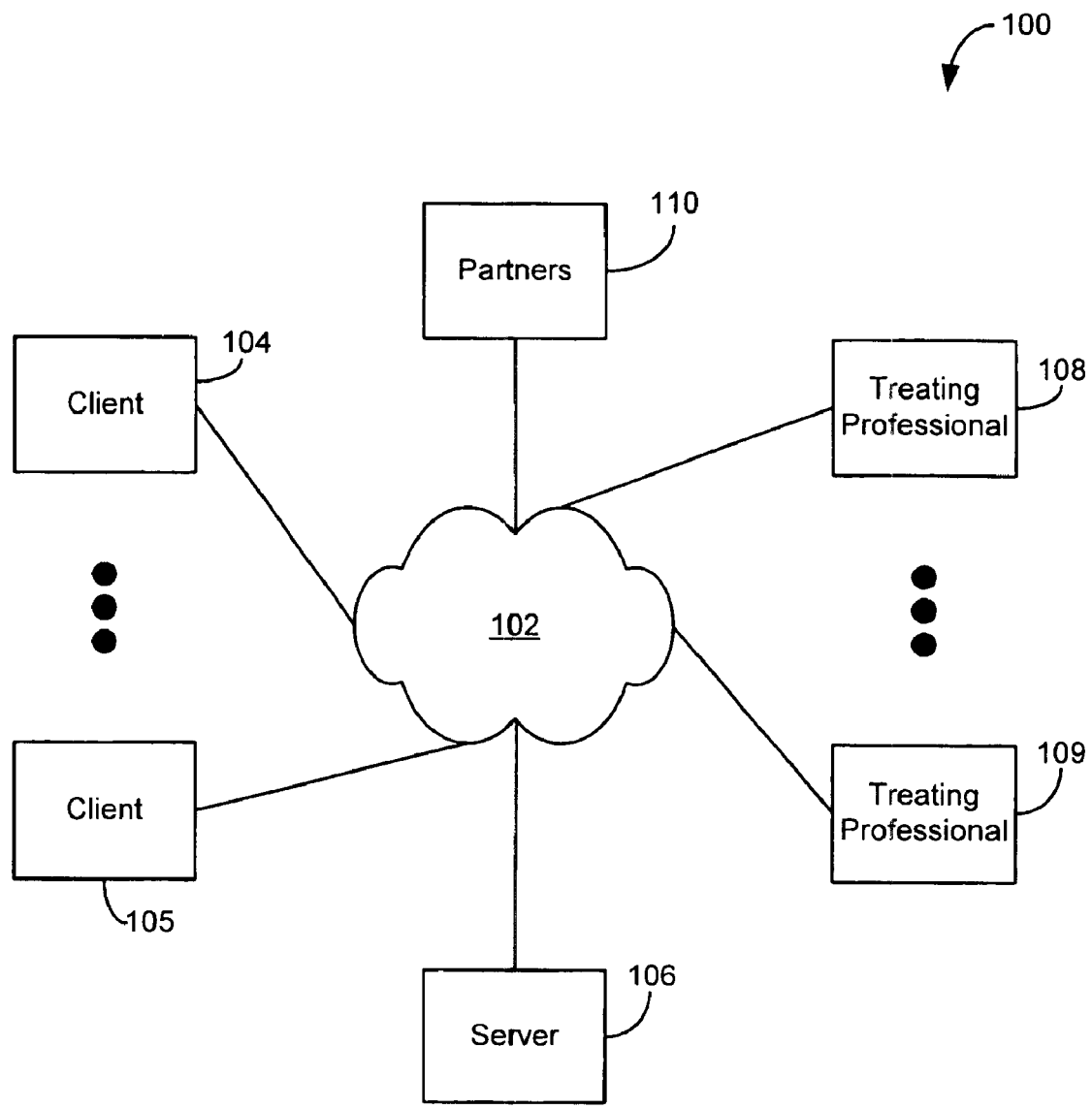
FIG. 1 is a diagram of an exemplary environment supporting electronic commerce.

Referring now to FIG. 1, an environment supporting a dental system 100 is shown. The system 100 communicates over a network 102 that can be a local area network or a wide area network such as the Internet.

One or more client computers 104-105 can be connected to the network 102. In one embodiment where the network 102 is the Internet, the client computers execute a suitable browser such as Navigator from Netscape, Inc. and Internet Explorer from Microsoft Corp. By clicking on the highlighted text (or specific graphic image), the user can jump from the current web page to a new web page address associated with the link—with the new page displayed on the screen. In this manner, the user can "surf the web" by clicking on an almost endless succession of links going to page after page all following a common thread as defined by the text or graphic component of the link label.

Through the network 102, the client computers 104-105 can access a dental server 106. The dental server 106 serves a web site, a portal, a vortal, or a content site for providing dental related information to interested parties such as dental patients, dentists, orthodontists, and others. When sensitive information is communicated through the dental server 106, such information is securely encrypted using Secure Sockets Layer (SSL) technology throughout the transaction. The server 106 can be a stand-alone computer or can be a server farm that can distribute processing and communications activity across a computer network so that no single device is overwhelmed. During load balancing, if one server is swamped with requests, excess requests are forwarded to another server with more capacity.

The network 102 connects the dental server 106 to one or more treating professional workstations 108-109. The workstations 108-109 allow treating professionals access to a plethora of services provided by the dental server 106 such as patient treatment and office management, among others. The dental server 106 stores information associated with patient history on-line in a secure manner. The server 106 also allows the treating professional to have a comprehensive view of the patient's treatment history at any time using a suitable browser, eliminating the need to pull treatment files or charts or to look for misfiled or lost charts. The dental server 106 also provides treating professionals with tools to analyze patient data, for example, tools to reconstruct a 3D model of the teeth. For example, using the browser, the treating professional can request the server 106 to animate the progress of the treatment plan. When the treating professional arrives at a prescription or other final designation, the treatment prescription is used to automatically generate appliances, as described in more details below. Further, in addition to aiding professionals in treating patients, the treating professional can perform office management, purchasing and other logistical operations using the browser and the dental server 106.

In addition to communicating with patients and treating professionals, the dental server 106 can communicate with one or more partners 110 using the network 102. The partners 110 can be product suppliers, service providers, or any suitable commercial entities.

One partner 110 can be a financing partner that offers customers with one or more electronic financing options. In one implementation, the financing partner can be a credit card processing company. The credit card processing company can accept a customer's existing credit card or can issue the customer with a new credit card. Further, the credit card can be issued under the name of a third-party bank, the name of the credit card processing company, or the name of the site supported by the dental server 106 under a co-branding arrangement.

The customer enters the sensitive data such as credit card number, shipping address, among others, onto a purchase form. The credit data is then submitted, collected and passed securely through the dental server 106. This data can be processed in real time or can be collected by mail or telephone and then entered by an operator. A processor at the credit card processing company then verifies that the credit card number is valid and is not stolen, among other anti-fraud measures. If the credit card information is valid, the purchase price will be reserved from the issuing bank of the consumer's credit card and allocated to the account associated with the server 106. Periodically, the credit card processor settles all accounts; it is at this time that all monies move. Funds reserved are transmitted from the issuing bank of the cardholder's credit card to the account of the server 106. Also, discount fees are paid from these funds, as they are moving.

Alternatively, the financing partner can debit from the customer's checking account over the Internet. One such check debiting services is the MerchanTrust™ Paperless Checks™ Services, available from Merchant Commerce, Inc. These services provide customers with the convenience of making online purchases by checking account debits, with no manual data entry required of a merchant. In this embodiment, a customer fills in a form at the site with bank information printed at the bottom of his or her personal check. The information is processed as an Electronic Funds Transfer (EFT) to the customer's account using the Automated Clearinghouse (ACH) payment system.

Yet another possible partner 110 is a dental supply retailer providing an on-line shop on the web site to retail dental products to the customers and treating professionals. The retailer can be a co-branding partner that uses the brand name linked or suitably associated with the web site of the server 106 such that users of the server 106 would not know that the on-line shop is actually operated by a third party. The retailer can offer dental products for brushing, flossing, and cleaning of dental implants and bridges. Other dental products include anti-plaque rinse and plaque-fighting toothpaste. The retailer can also sell other health-care-related products such as prescription drugs; non- prescription drugs; personal care; beauty and spa; vitamins, herbs and nutrition; and medical supplies. Additionally, the retailer can serve the needs of the treating professionals by offering products such as brackets, buccal tubes, bands, archwire products, bonding adhesives, hand instruments, systems, supplies and equipment.

Yet another partner 110 can be a shipping partner. The shipping partner delivers dental supply or goods received from a multiplicity of producers and manufacturers for ultimate distribution to each customer. The facilities for warehousing and introduction of goods into a transportation stream for redistribution are the so-called cross docking facilities. The supply or good flows in bulk from a producer or a manufacturer to one or more cross docking facilities owned by either the shipping partner or the operator of the server 106. The items are then be broken into smaller unit sizes and distributed to the customers.

The above list of partners lists only exemplary partners and is not an exhaustive list. Other possible partners include value-added service providers such as third party software providers who provide plug-in viewing and diagnostic enhancements that can be used by the professionals.

The server 106 can perform dynamic targeting and information gathering. The users provide demographic information when they register for our service. The server 106 can track our users' behavior the entire time they are online. As a result, the server 106 can deliver targeted advertisements and measure their effectiveness. For example, users can receive ads from a brokerage firm when they are viewing sites containing stock quotes or financial news, or receive promotions from a bookseller when browsing sites containing book reviews. As such, the dental server 106 can provide a prominent and sustained advertising medium to the community. In contrast to most portal and content sites which display advertising, the site remains with users the entire time they are online. Once users are logged on, the site remains in full view throughout the session, including when they are waiting for pages to download, navigating the Internet and even engaging in non-browsing activities such as sending or receiving e-mail. The constant visibility of the site allows advertisements to be displayed for a specified period of time.

In combination, the dental server 106 forms a hub that links dental clients using client computers 104-105, treating professionals using workstations 108-109, and partners 110 into a living electronic commerce (e-commerce) community.

Figure 2:
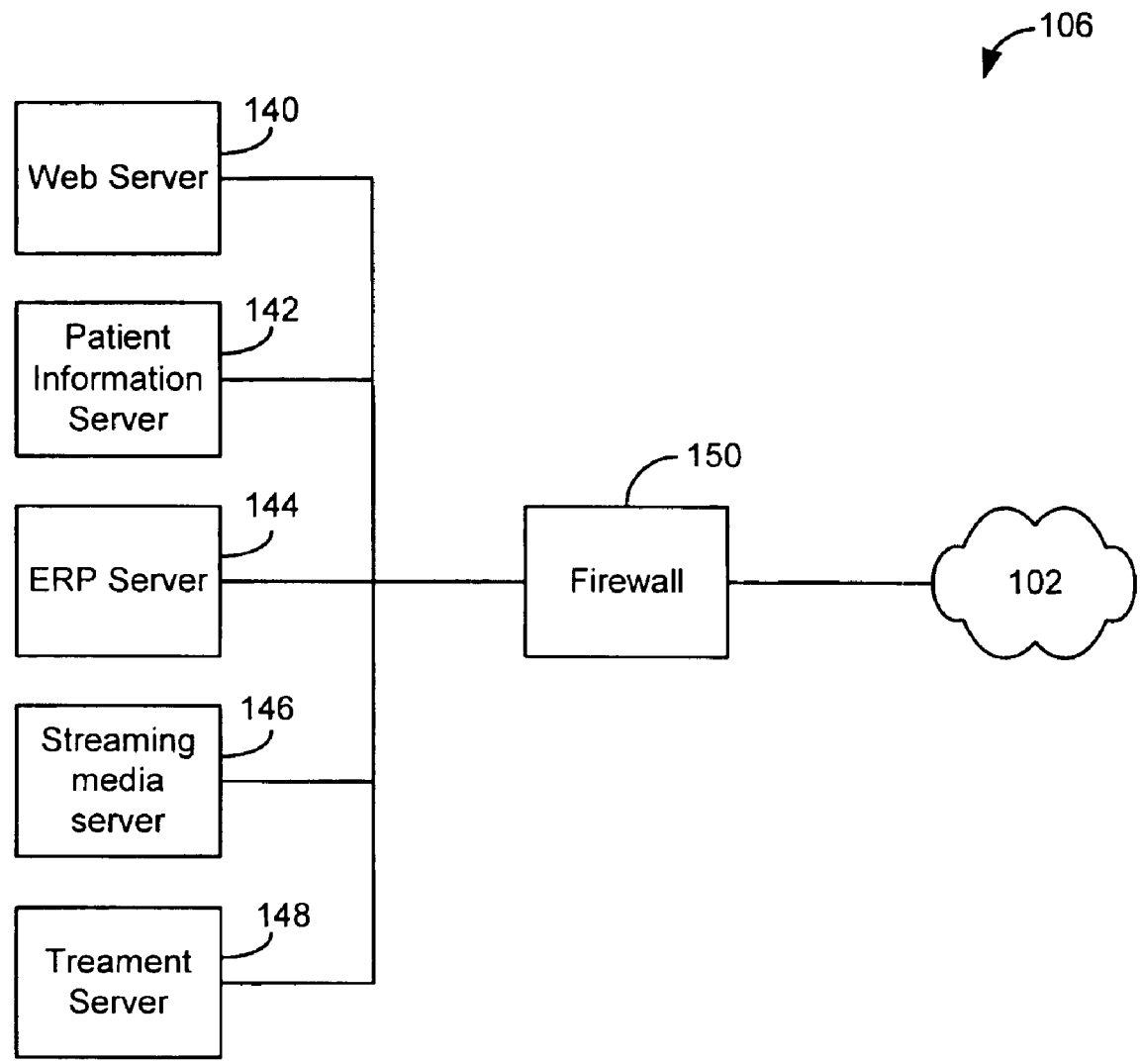
FIG. 2 is a diagram of a server to support electronic commerce.

FIG. 2 shows an embodiment of the server 106. The server 106 includes a web server 140, a patient information server 142, a resource planning (RP) server 144 and a streaming server 146. In one embodiment, the RP server 144 runs Microsoft SQL server and provides information relating to a doctor or a patient such as address and history. When a patient's case or static snapshots of the case is needed, the data is pulled from the patient information server 142. When media data such as video needs to be streamed to a requesting client, the streaming server 146 can send the stream. In one implementation, the streaming data is stored in QuickTime format on a Linux-based server running the QuickTime server software.

The servers can be clustered. In one embodiment using Microsoft's Cluster Server, cluster-enabled applications such as Microsoft's SQL Server and Exchange. With Cluster Server, two servers can run applications at the same time. When one server fails, the remaining server handles its application as well as the failed server's applications. Next, the remaining server adopts the IP address of the failed server and mounts one or more data drives that the two systems share. The remaining server is rebooted and applications such as SQL Server can be started and initialized on this server. Persistent clients can re-attach to the server and continue to operate.

Figure 3:
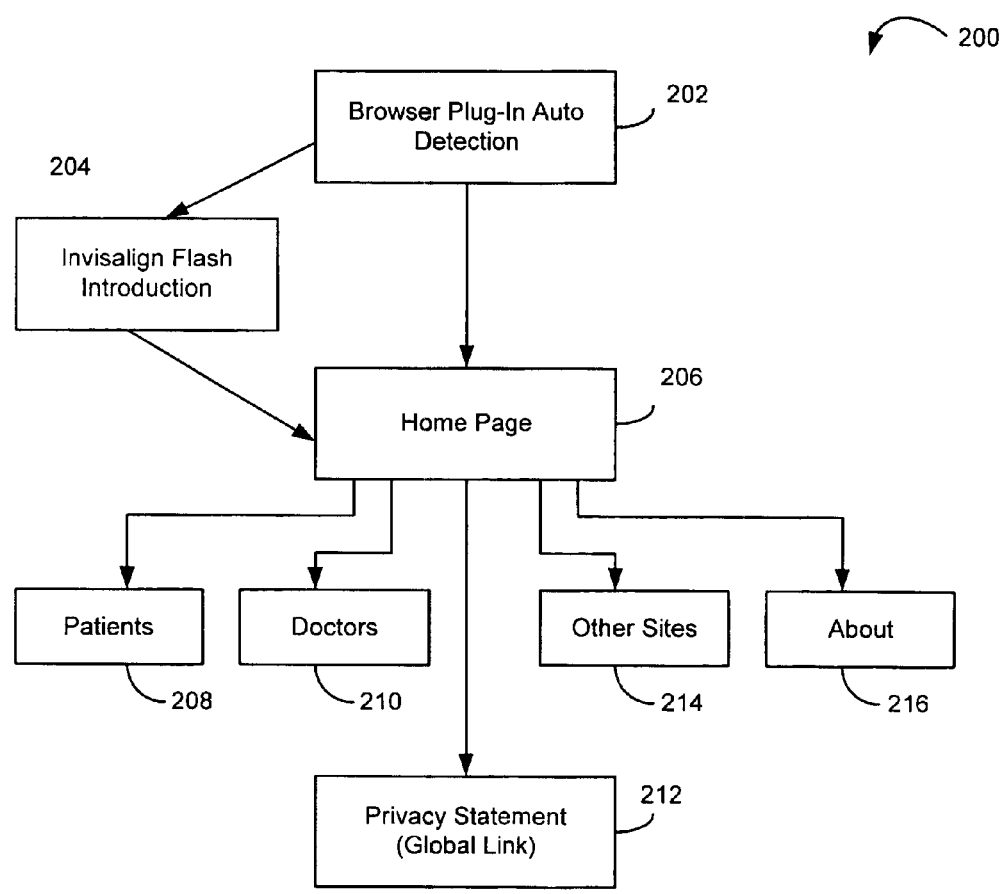
FIG. 3 is a diagram of a web site on the server of FIG. 2.

Referring now to FIG. 3, a diagram 200 shows various major functions supported by the dental server 106. First, the process 200 performs an automatic detection for the existence of a browser welcome plug-in (step 202). If the welcome plug-in exists, an introductory animation (flash) is shown (step 204). From step 204 or 206, the process 200 shows a home page (step 208) with one or more links. A link is created by having a word in a text field (or a graphic image on a web page) linked to the location of another web page, via a string of information setting forth the new web page address presented in hypertext transfer protocol (HTTP), among others.

The user can navigate the home page to join a particular site from a constellation of related sites. For instance, the user can navigate to a patient's site (step 208), a doctor's site (step 210), a privacy statement site (step 212), one or more additional sites (step 214), and an about site (step 216), among others. The additional sites can be an on-line shopping store that is co-branded with the web site hosted by the server 106, or the on-line shopping store can be directly affiliated with a third party such as planet-rx.com, among others. The additional sites can also be third party value-added providers of products and/or services.

Figure 4:
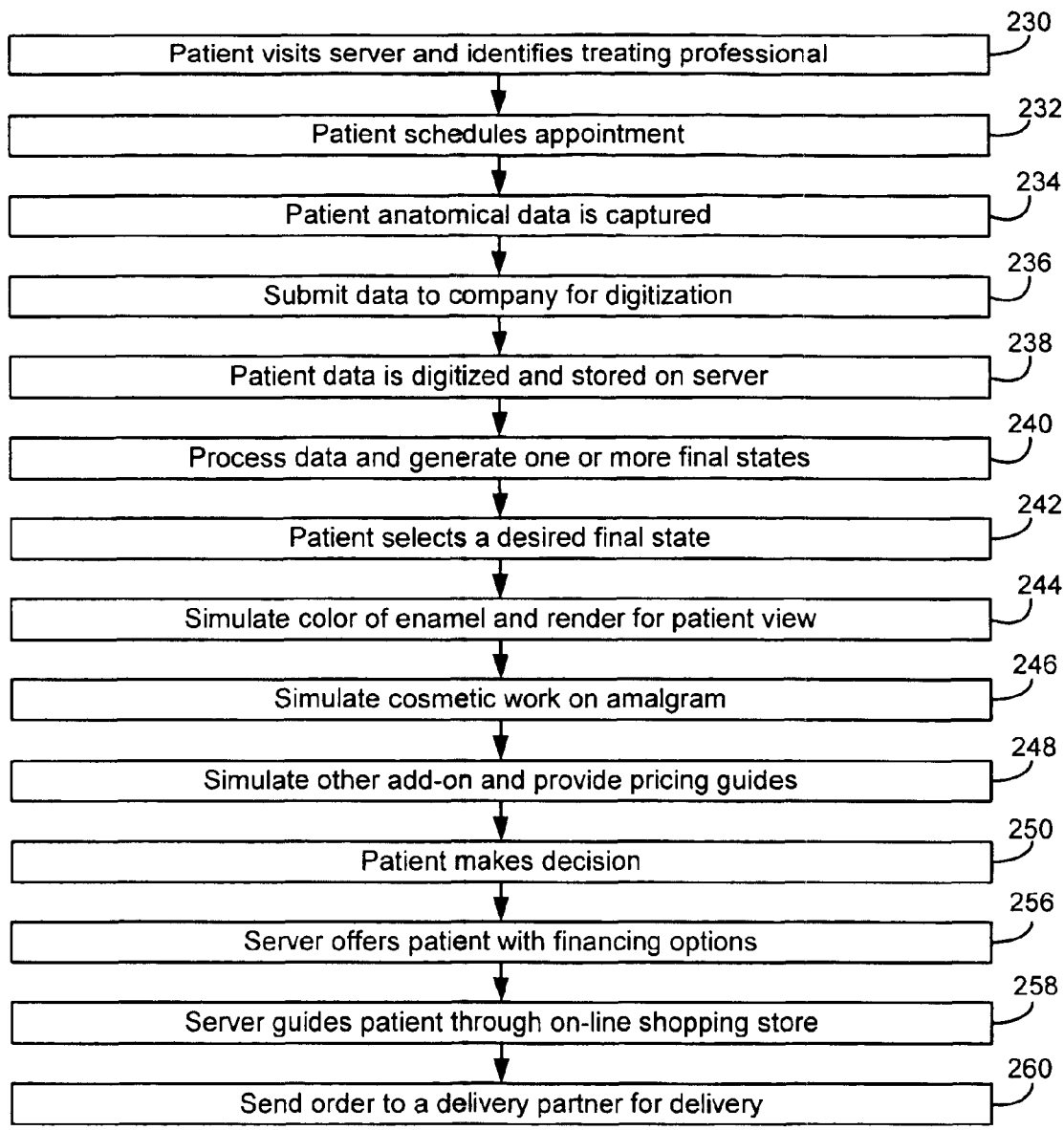
FIG. 4 is a flowchart of a process for selecting dental services from a patient's perspective.
Figure 5:
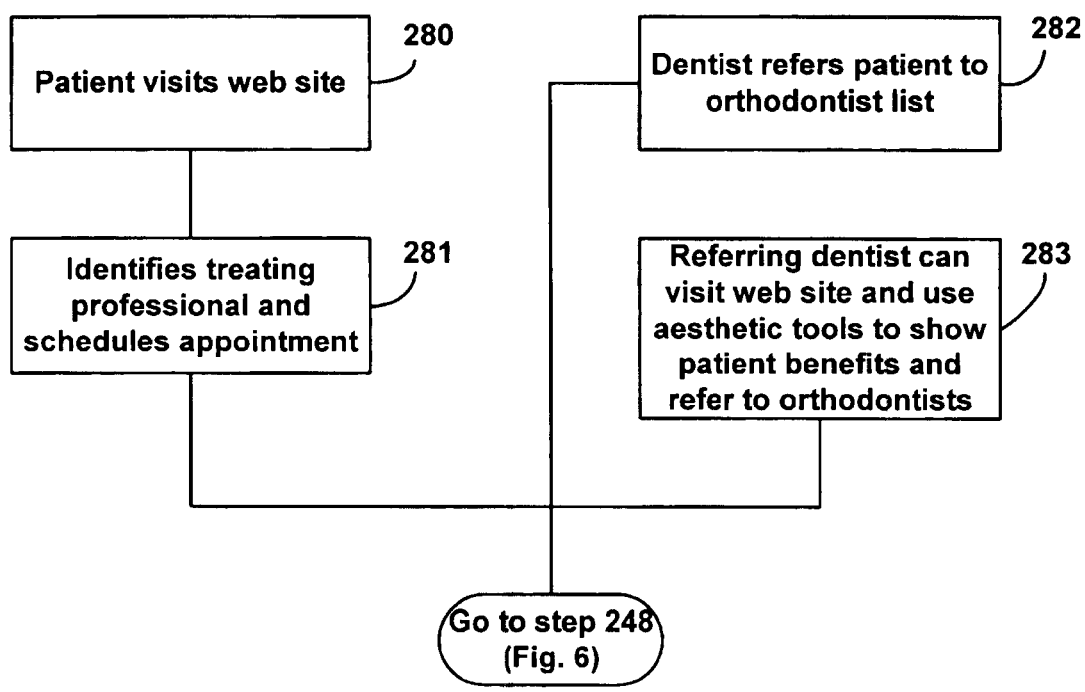
FIG. 5 is a flowchart of a first process for providing dental services from a treating professional's perspective.
Figure 6:
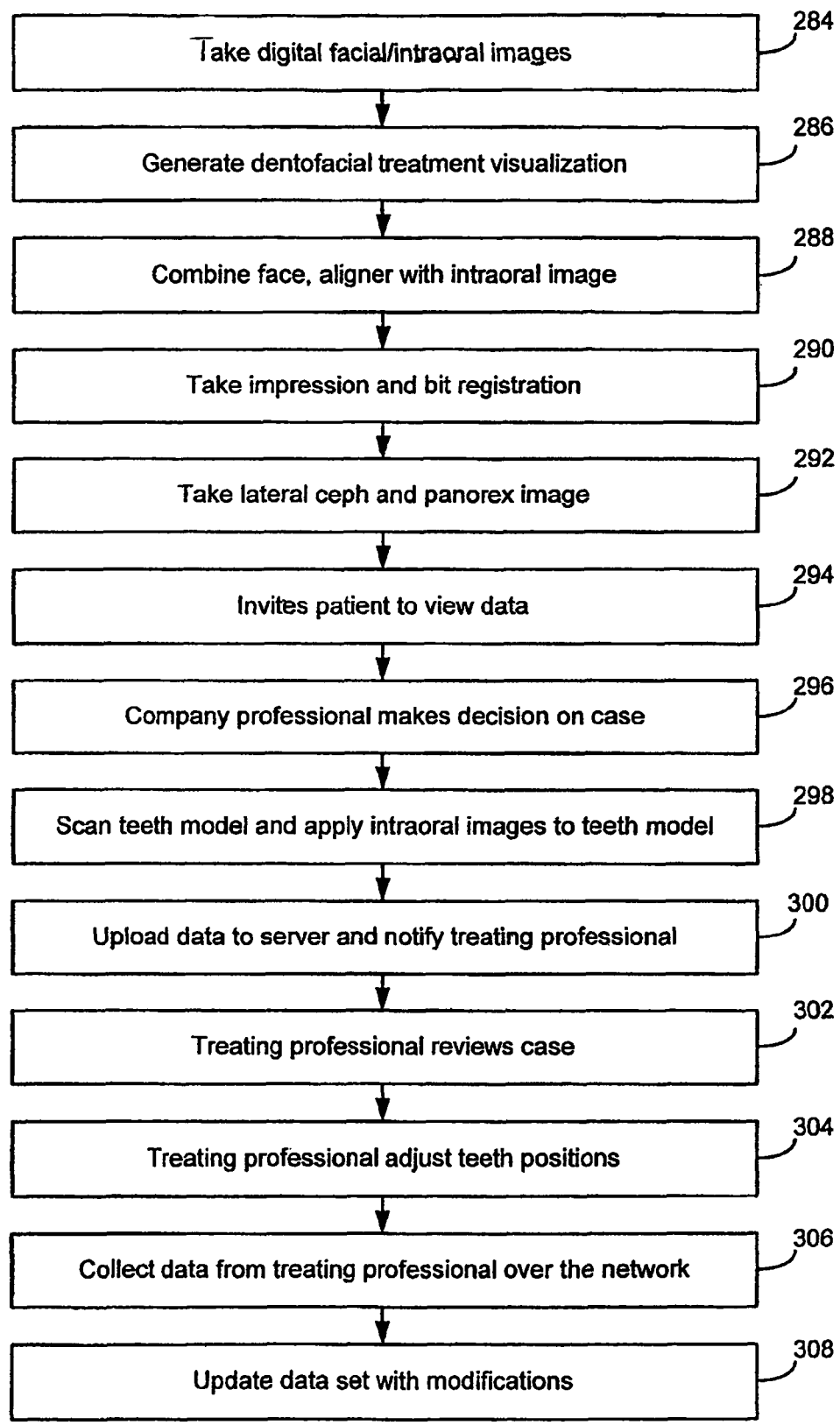
FIG. 6 is a flowchart of a second process for providing dental services from a treating professional's perspective.

FIG. 4 illustrates an exemplary usage of the system of FIG. 1 from a patient's perspective. First, a prospective client using a client computer 104 visits the web site on the dental server 106 and identifies a treating professional meeting one or more criteria, for example a professional whose location is closest to his or her home address (step 230). Next, the patient schedules an appointment with the treating professional (step 232). At the meeting, an assistant captures various anatomical data from the patient by taking digital photographs of the face and teeth, taking x-rays of the front, back, side, and top/bottom of the patient, taking one or more impressions, among others (step 234). Next, this information is entered into a form on the server 106 (step 236). The data is then digitized, stored on the server 106, and made available to the treating professionals and the patient over the Internet (step 238). Next, the server 106 and one or more orthodontic treating persons process the patient data and render the patient's teeth in a plurality of alternative final states (step 240). Based on the choices, the patient selects a desired final state (step 242).

In addition to performing orthodontic operations, the server 106 can also perform other value-added services. For example, processes executed by the server 106 can simulate the color of the patient's enamel and show the color of the teeth before and after bleaching (step 244). Further, processes on the server 106 can simulate the color of the patient's silver fillings (amalgram) and show the teeth after cosmetic work to cover the amalgam (step 246). After visualizing the effects of the operations, comparing the before and after operations, and reviewing guideline pricing for the orthodontic operation as well as add-ons such as bleaching (step 248), the patient makes a decision (step 250).

Once the patient has accepted a particular treatment selection, the server 106 offers the patient with one or more financing options from one of its financial partners (step 256). Additionally, the server 106 can guide the patient to an on-line shopping store to purchase products relating to his or her dental health (step 258). For example, the patient can buy cleaning supplies, brushes, and flossing supply at a price competitive to his or her traditional stores. Moreover, the products can be delivered to the patient using one or more delivery partners at a convenient time (step 260).

FIG. 4 illustrates an exemplary usage of the system of FIG. 1 from a treating professional's perspective. A prospective patient uses a client computer 104 and visits the web site on the dental server 106 (step 280). The client identifies a treating professional and schedules an appointment with the treating professional (step 281). Alternatively, a referring dentist can refer the client to the treating orthodontist (step 282). The referring dentist can visit the web site on the dental server 106 and uses one or more dental esthetic tools to show patients the potential benefits of anterior and posterior esthetic restorations and, if the patient is interested, refers the patient to the treating professional (step 283).

During an initial examination, the treating professional or an assistant takes a set of digital facial and intraoral images which is uploaded to a secure, collaborative workspace on the dental server 106 (step 284). The workspace is shared with the referring dentist.

Next, the treating professional generates a dentofacial treatment visualization showing the patient's face and smile before and after treatment (step 286). The treating professional can also combine the patient's face and an aligner into the intraoral image to show how the inconspicuous the appliance will be (step 288).

Once the patient requests treatment, the treating professional takes impressions and a bite registration and sends the information to the company (step 290). The treating professional also takes a lateral ceph and a panorex and uploads them and a treating prescription to the workspace (step 292). The professional's assistant creates a separate workspace for the patient, uploads selected "before and after" images into it, and invites the patient to review the images (step 294).

At the company, another professional reviews the records and decides to accept or decline the case (step 296). The models are then scanned, and the intraoral images are retrieved and used to texture-map enamel and gingiva (step 298). The data is then sent to the workspace and the treating professional is notified (step 300).

In one embodiment, the tooth models may be posted on a hypertext transfer protocol (http) web site for limited access by the corresponding patients and treating clinicians. Since realistic models have a large volume of data, the storage and transmission of the models can be expensive and time consuming. To reduce transmission problems arising from the large size of the 3D model, in one embodiment, data associated with the model is compressed. The compression is done by modeling the teeth meshes as a curve network before transmission to the treating professional. Once the curve network is received, the 3D model is reconstructed from the curve network for the treating professional to analyze. More information on the compression is disclosed in a co-pending application having Ser. No. 09/50,6419, filed Feb. 17, 2000, (now U.S. Pat. No. 6,463,344) entitled, "EFFICIENT DATA REPRESENTATION OF TEETH MODEL", and filed by ELENA PAVLOVSKAIA and HUAFENG WEN, the contents of which are hereby incorporated.

The treating professional can, at his or her convenience, check the setup, and review the information sent in step 300 (step 302). The treating professionals can use a variety of tools to interpret patient information. For example, the treating professional can retrieve and analyze patient information through a reconstructed 3D model of the patient's teeth and other anatomical structures. The professional can view animations showing the progress of the treatment plan to help the treating physician visualize the pace of treatment. Using these tools, the treating professional can easily and quickly view and/or edit the treatment plan.

If necessary, the treating professional can adjust one or more teeth positions at various intermediate stages of treatment (step 302). A variety of diagnostic decision-support capabilities such as automated teeth collision detection can be used to aid the treating professional in adjusting the teeth positions.

When the treating professional arrives at a prescription or other final designation, the treatment information is automatically collected by the system over the Internet, thus eliminating the cost and delay associated with the traditional physical shipping of patient information (step 304). These modifications are then retrofitted onto the dataset used to generate the aligners (step 306).

Figure 7:
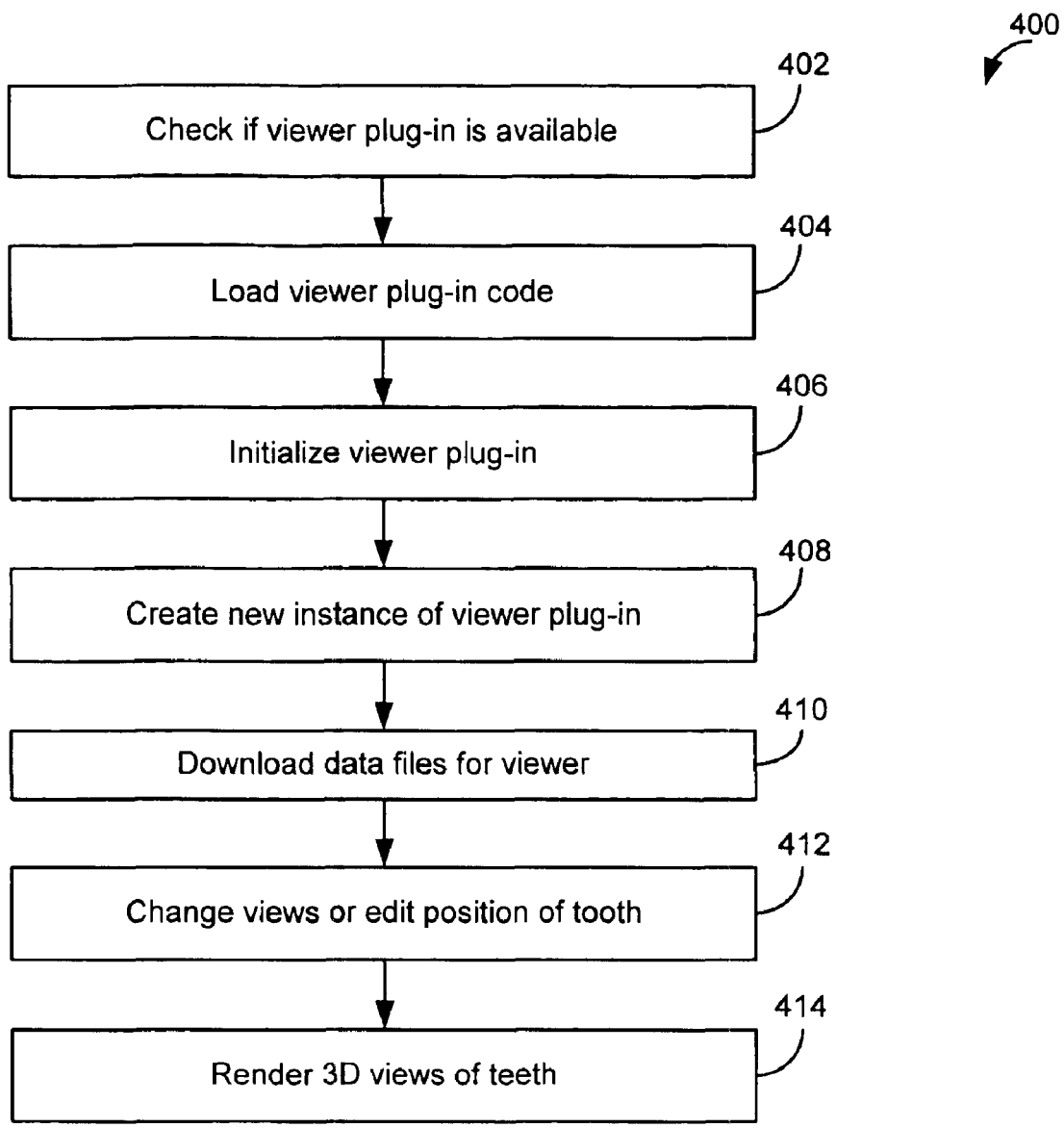
FIG. 7 is a flowchart of a process to render 3D views of a patient's teeth on a browser.
Figure 8:
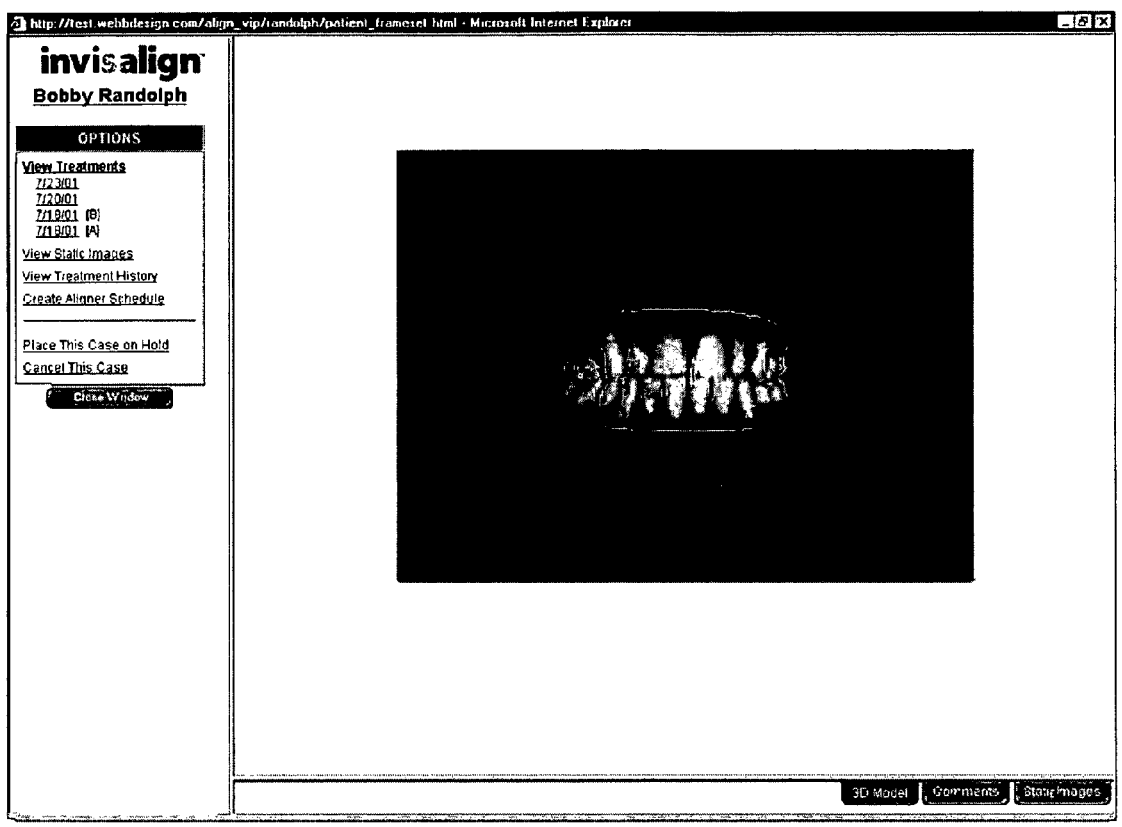
FIG. 8 is an exemplary output of the process of FIG. 7 using the browser.

FIG. 7 shows a process 400 associated with a viewer that allows the treating professional to visualize the patient's teeth over the network 102 such as the Internet. In one embodiment, during start-up, a browser checks for a viewer plug-in module embodying the process 400 in a "plugins" subdirectory (Windows) or Plug-ins folder (Mac OS) in the same folder or directory as the browser (step 402). If the viewer plug-in module is available, the browser looks for a MIME type and extension info from the version resource. Through a TYPE attribute, the browser knows the MIME type and can load a registered plug-in first and, if there are no matches for the MIME type, the browser looks for a helper application.

Once the viewer plug-in is identified, the browser loads the viewer plug-in code into memory (step 404); initializes the viewer plug-in (step 406); and creates a new instance of the viewer plug-in (step 408). When the professional leaves the site or closes the window, the viewer plug-in instance is deleted. When the last instance of the viewer plug-in is deleted, the plug-in code is unloaded from memory.

Next, data files are downloaded to the viewer plug-in (step 410). In one implementation, the viewer plug-in downloads a data file from the dental server 102 using a suitable protocol such as a file transfer protocol (FTP). The viewer plug-in uses the downloaded file to present the treatment plan graphically to the clinician. The viewer plug-in also can be used by the treatment plan designer at the host site to view images of a patient's teeth. FIG. 4 shows an exemplary user interface for the viewer plug-in of FIG. 3. The professional can change views, select a particular tooth and change its position as desired (step 412).

3-D images of various orthodontic views can then be rendered after each instruction from the treating professional is received (step 414). In this process, an origin point, or "look from" point associated with a camera view is generated. Next, a "look at" point or a focus point associated with the camera view is determined. In this system, the line from LookFromPoint to LookAtPoint defines the direction the camera is shooting at. Additionally, a camera Z vector, or up vector, is determined.

Figure 9:
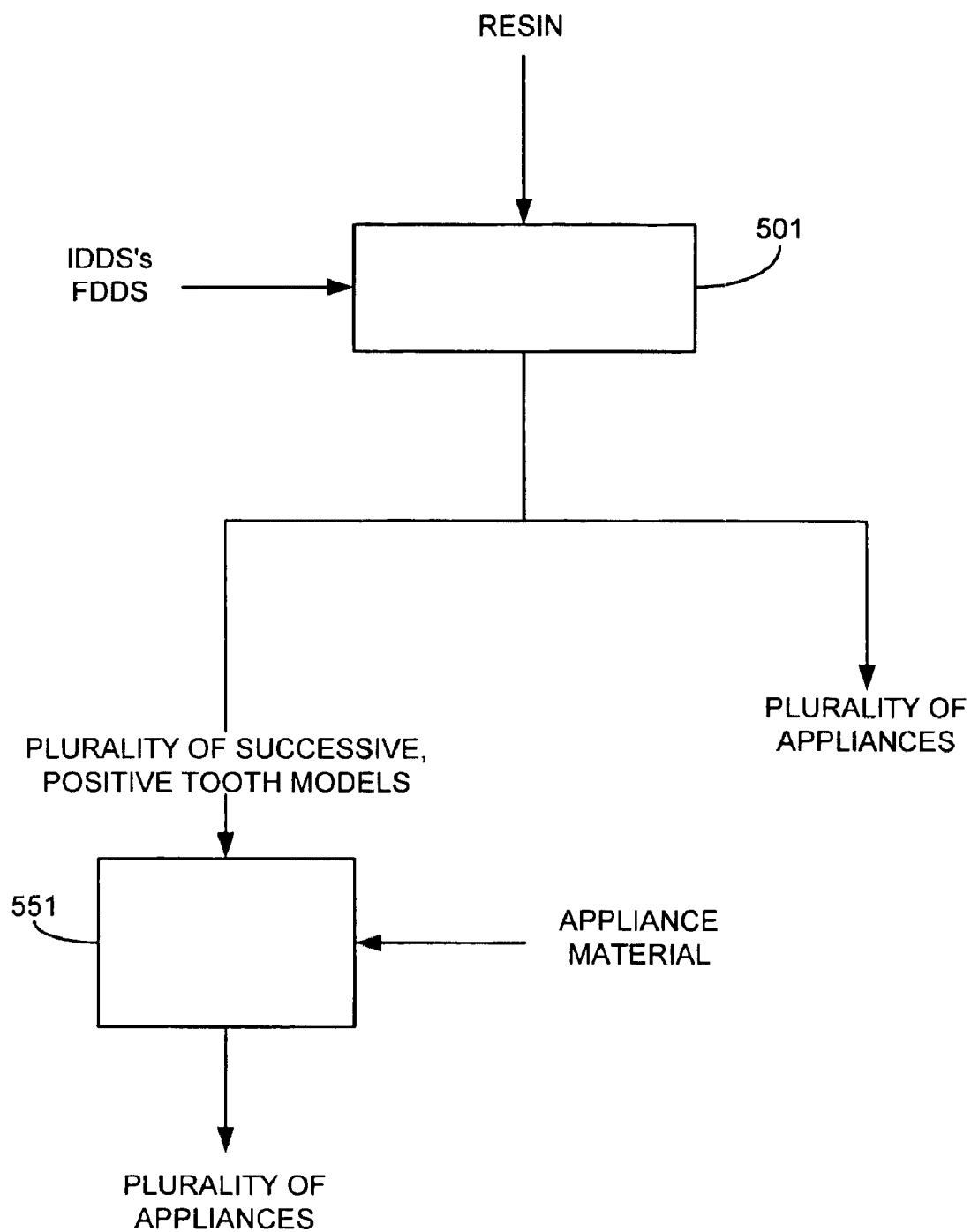
FIG. 9 is a diagram of a system for manufacturing appliances.

Exemplary pseudo code implementations for generating various orthodontic views is shown below. With reference to the pseudo code, the code defines a bounding box of one mold (2 arches) which is the smallest cube containing the molds geometry. Other settings associated with the bounding box include:

Z_Axis: point from lower to upper,
Y_Axis: point from inside mouse to front teeth (incisors)
X_Axis: point from center to left.
FieldOfView: is the open angle, it corresponding to lens
HalfFieldOfView: FieldOfView*0.5
MoldCenter: Center of the BoundingBox
X_Length: BoundingBox X dimension
Y_Length: BoundingBox X dimension
Z_Length: BoundingBox X dimension
X_MIN: minimum X value of the BoundingBox i.e. right most surface cube X value.
X_MAX: maximum X value of the BoundingBox
Y_MIN: minimum Y value of the BoundingBox
Y_MAX: maximum Y value of the BoundingBox
Z_MIN: minimum Z value of the BoundingBox
Z_MAX: maximum Z value of the BoundingBox
Right Buccal Overjet View Pseudo-Code
CameraLookFromPoint:
X=0.5*MoldCenter.X+0.5*X_Max+0.25*MAX
  (Y_Length, Z_Length)/tan(HalfFieldOfView);
Y=MoldCenter.Y
Z=MoldCenter.Z−0.25*MAX(Y_Length, Z_Length)/tan
  (HalfFieldOfView);
CameraLookAtPoint:
X=MoldCenter.X+0.25*X_Length;
Y=MoldCenter.Y;
Z=MoldCenter.Z;
CameraUpVector: ZAxis;
Anterior Overjet View Pseudo-Code
CameraLookFromPoint:
X=MoldCenter.X;
Y=0.5*MoldCenter.Y+0.5*Y_Max+0.25*MAX
  (X_Length, Z_Length)/tan(HalfFieldOfView);
Z=MoldCenter.Z−0.25MAX(X_Length, Z_Length)/tan
  (HalfFieldOfView);
CameraLookAtPoint:
X=MoldCenter.X;
Y=MoldCenter.Y+0.25*Y_Length;
Z=MoldCenter.Z;
CameraUpVector: ZAxis;
Left Buccal Overjet View Pseudo-Code
CameraLookFromPoint:
X=0.5*MoldCenter.X+0.5*X_Min−0.25*MAX
  (Y_Length, Z_Length)/tan(HalfFieldOfView);
Y=MoldCenter.Y;
Z=MoldCenter.Z−0.25*MAX(Y_Length, Z_Length)/tan
  (HalfFieldOfView);
CameraLookAtPoint:
X=MoldCenter.X−0.25*X_Length;
Y=MoldCenter.Y;
Z=MoldCenter.Z;
CameraUpVector: ZAxis;
Left Distal_Molar
CameraLookFromPoint:
X=MoldCenter.X−0.25*X_Length;
Y=Y_Min−0.25*MAX(X_Length, Z_Length)/tan
  (HalfFieldOfView);
Z=MoldCenter.Z;
CameraLookAtPoint:
X=MoldCenter.X−0.25*X_Length;
Y=MoldCenter.Y;
Z=MoldCenter.Z;
CameraUpVector: ZAxis;

Left Lingual View Pseudo-Code
CameraLookFromPoint:
X=MoldCenter.X+0.125*X_Length;
Y=MoldCenter.Y;
Z=MoldCenter.Z;
CameraLookAtPoint:
X=MoldCenter.X−0.25*X_Length;
Y=MoldCenter.Y;
Z=MoldCenter.Z;
CameraUpVector: ZAxis;
Lingual Incisor View Pseudo-Code
CameraLookFromPoint:
X=MoldCenter.X;
Y=MoldCenter.Y;
Z=MoldCenter.Z;
CameraLookAtPoint:
X=MoldCenter.X;
Y=MoldCenter.Y+0.25*Y_Length;
Z=MoldCenter.Z;
CameraUpVector: ZAxis;
Right Lingual View Pseudo-Code
CameraLookFromPoint:
X=MoldCenter.X+0.125*X_Length;
Y=MoldCenter.Y;
Z=MoldCenter.Z;
CameraLookAtPoint:
X=MoldCenter.X+0.25*X_Length;
Y=MoldCenter.Y;
Z=MoldCenter.Z
CameraUpVector: ZAxis;
Right Distal Molar View Pseudo-Code
CameraLookFromPoint:
X=MoldCenter.X+0.25*X_Length;
Y=Y_MIN−0.25*MAX(X_Length, Z_Length)/tan(HalfFieldOfView);
Z=MoldCenter.Z;
CameraLookAtPoint:
X=MoldCenter.X+0.25*X_Length;
Y=MoldCenter.Y;
Z=MoldCenter.Z;
CameraUpVector: ZAxis;

Once the intermediate and final data sets have been created, the appliances may be fabricated as illustrated in FIG. 9. Common fabrication methods employ a rapid prototyping device 501 such as a stereolithography machine. A particularly suitable rapid prototyping machine is Model SLA-250/50 available from 3D System, Valencia, Calif. The rapid prototyping machine 501 selectively hardens a liquid or other non-hardened resin into a three-dimensional structure which can be separated from the remaining non-hardened resin, washed, and used either directly as the appliance or indirectly as a mold for producing the appliance. The prototyping machine 501 receives the individual digital data sets and produces one structure corresponding to each of the desired appliances. Generally, because the rapid prototyping machine 501 may utilize a resin having non-optimum mechanical properties and which may not be generally acceptable for patient use, the prototyping machine typically is used to produce molds which are, in effect, positive tooth models of each successive stage of the treatment. After the positive models are prepared, a conventional pressure or vacuum molding machine 551 is used to produce the appliances from a more suitable material, such as 0.03 inch thermal forming dental material, available from Tru-Tain Plastics, Rochester, Minn. 55902. Suitable pressure molding equipment is available under the trade name BIOSTAR from Great Lakes Orthodontics, Ltd., Tonawanda, N.Y. 14150. The molding machine 551 produces each of the appliances directly from the positive tooth model and the desired material. Suitable vacuum molding machines are available from Raintree Essix, Inc.

After production, the appliances can be supplied to the treating professional all at one time. The appliances are marked in some manner, typically by sequential numbering directly on the appliances or on tags, pouches, or other items which are affixed to or which enclose each appliance, to indicate their order of use. Optionally, written instructions may accompany the system which set forth that the patient is to wear the individual appliances in the order marked on the appliances or elsewhere in the packaging. Use of the appliances in such a manner will reposition the patient's teeth progressively toward the final tooth arrangement.

Because a patient's teeth may respond differently than originally expected, the treating clinician may wish to evaluate the patient's progress during the course of treatment. The system can also do this automatically, starting from the newly-measured in-course dentition. If the patient's teeth do not progress as planned, the clinician can revise the treatment plan as necessary to bring the patient's treatment back on course or to design an alternative treatment plan. The clinician may provide comments, oral or written, for use in revising the treatment plan. The clinician also can form another set of plaster castings of the patient's teeth for digital imaging and manipulation. The clinician may wish to limit initial aligner production to only a few aligners, delaying production on subsequent aligners until the patient's progress has been evaluated.

Figure 10:
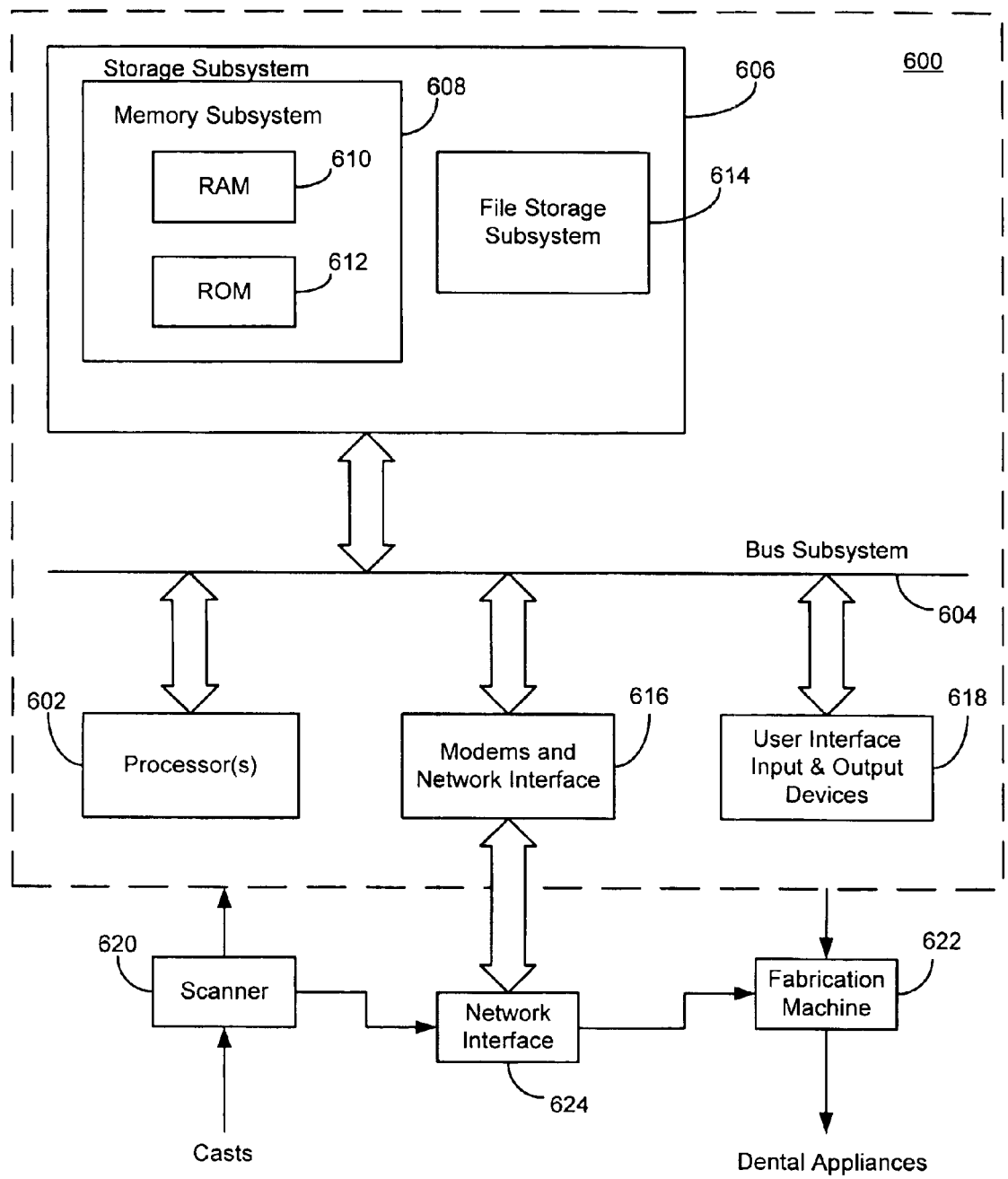
FIG. 10 is a diagram illustrating a computer system to support the fabrication of appliances.

FIG. 10 is a simplified block diagram of a data processing system 600 that may be used to develop orthodontic treatment plans. The data processing system 600 typically includes at least one processor 602 that communicates with a number of peripheral devices via bus subsystem 604. These peripheral devices typically include a storage subsystem 606 (memory subsystem 608 and file storage subsystem 614), a set of user interface input and output devices 618, and an interface to outside networks 616, including the public switched telephone network. This interface is shown schematically as "Modems and Network Interface" block 616, and is coupled to corresponding interface devices in other data processing systems via communication network interface 624. Data processing system 600 could be a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display, or a three dimensional pointing device, such as the gyroscopic pointing device described in U.S. Pat. No. 5,440,326, other types of user interface input devices, such as voice recognition systems, can also be used.

User interface output devices typically include a printer and a display subsystem, which includes a display controller and a display device coupled to the controller. The display device may be a cathode ray tube (CRT), a flat-panel device such as a liquid crystal display (LCD), or a projection device. The display subsystem may also provide non-visual display such as audio output.

Storage subsystem 606 maintains the basic required programming and data constructs. The program modules discussed above are typically stored in storage subsystem 606. Storage subsystem 606 typically comprises memory subsystem 608 and file storage subsystem 614.

Memory subsystem 608 typically includes a number of memories including a main random access memory (RAM) 610 for storage of instructions and data during program execution and a read only memory (ROM) 612 in which fixed instructions are stored. In the case of Macintosh-compatible personal computers the ROM would include portions of the operating system; in the case of IBM-compatible personal computers, this would include the BIOS (basic input/output system).

File storage subsystem 614 provides persistent (non-volatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected via various local-area or wide-area network media, including telephone lines. Similarly, the input devices and display need not be at the same location as the processor, although it is anticipated that personal computers and workstations typically will be used.

Bus subsystem 604 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 620 is responsible for scanning casts of the patient's teeth obtained either from the patient or from an orthodontist and providing the scanned digital data set information to data processing system 600 for further processing. In a distributed environment, scanner 620 may be located at a remote location and communicate scanned digital data set information to data processing system 600 via network interface 624.

Fabrication machine 622 fabricates dental appliances based on intermediate and final data set information received from data processing system 600. In a distributed environment, fabrication machine 622 may be located at a remote location and receive data set information from data processing system 600 via network interface 624.

The system of the present invention is a web-based transaction environment that allows qualified orthodontists and dental practitioners to submit malocclusion cases as candidates for treatment. The system is also used for managing the cases accepted for treatment. The treating professional can accomplish the case submission and case management process entirely within the web-based environment. An orthodontist or treating professional submits cases into a case submission system. The treating professional can also view and manage the case using a case management system. The case management system also interacts with a provider, which operates the system of FIG. 9 in producing aligners for patients based on instructions from the treating professional.

Case submission is the process of creating and submitting a malocclusion case as a candidate for the system's treatment, all within a web-based environment. The orthodontist or treatment professional initiates the case submission process by first logging in to the web application. After a successful login, the treating professional can begin the case creation process. The treating professional enters the patient information, their practice information, the billing and shipping information, and finally the diagnosis and treatment plan. After the case details are finished, the treating professional submits the case information. Subsequently, the treating professional can submit the associated digital images and x-rays. The submitted case is received by the provider. This completes the case submission process.

First, the user clicks on a Start a New Case link to take the user to an On-line Treatment Planning Form where the user can complete the On-line Treatment Planning form and submit the form.

First, the treating professional logs in. The doctor information is updated. Next, patient information is entered. The user can also enter billing information as well as shipping information. Next, the treating professional enters a diagnosis. The treating professional also enters the treatment plan. The case is then submitted. Additionally, digital photographs can be submitted and uploaded to the system of FIG. 10. Also, digital x-ray cells are submitted.

Once the user has submitted the On-line Treatment Planning Form, the user prints copies of the 'Treatment Planning Form Summary', save one copy for the user's records, and place the second copy in the Orthodontics Records box along with the same materials the user typically sends to the system. Next, the user prints a shipping label by clicking on the 'Print UPS Label' button that appears when the user submits a new case on-line. The shipping label is affixed to the outside of an orthodontics records box that contains a Treatment Planning Form Summary, a PVS impression of each arch in a separate foam bag, a bite registration in a separate foam bag, copies of the patient's x-rays, and copies of the patient's photos (intraoral and extraoral), for example.

Case management takes place after the treating professional has submitted the case. The case management process consists of the recursive review and approve process all taking place within the web environment. The case management process ends when the treating professional has finished the closed case.

First, the treating professional submits the case. The system receives the case over the network, and an experienced professional reviewer reviews the case. The completed review is submitted to the server and the treating professional can review and approve the case. Upon receiving the approval, the case manager accepts the case. The case is then forwarded to the system of FIG. 10 to develop a computer model. The computer model is then presented to the case manager, who in turn forwards the model to the treating professional for approval. The treating professional reviews and if he or she accepts the treatment plan, sends an approval to the case manager. The system of FIG. 9 then manufacturers the aligners. The produced aligners are then shipped to the treating professional. Upon receipt of the fabricated aligners, the treating professional can finish the case. Upon conclusion of treatment, the case is closed and the system of FIG. 10 sends an instruction to the case manager to close the case.

First, a new case is started. This can be done using a treatment planning form. The treatment planning form allows the user to select a case type and to evaluate orthodontic conditions that may be encountered. The process then captures doctor and patient information using a doctor and patient information form. This form verifies address information and shipping information, patient information, and allows the doctor to enter case refinement coverage options, among others. The doctor enters a diagnosis. This can be done through a diagnosis form. The doctor then enters the treatment goals. This can be done using a treatment goals form. The doctor then summarizes the case using a treatment plan summary preview. The case is submitted. This can be done using a treatment plan summary. A shipping label is printed using for example, a UPS label printing process for cases that are shipped using UPS.

First, a user logs in. In this process, doctor information can be processed. Next, a new case can be started. In this step, case type information can be collected, patient information data can be collected, diagnosis information can be collected, or treatment goals can be collected. The case can be submitted. This can be done over the network. Additional case submission information can also be submitted. X-ray information includes PVS impression, wax bite, x-rays, and digital images, among others. The information from the case submitted and the case submission data is then reviewed. The reviewer can modify, accept, or reject.

Figure 11:
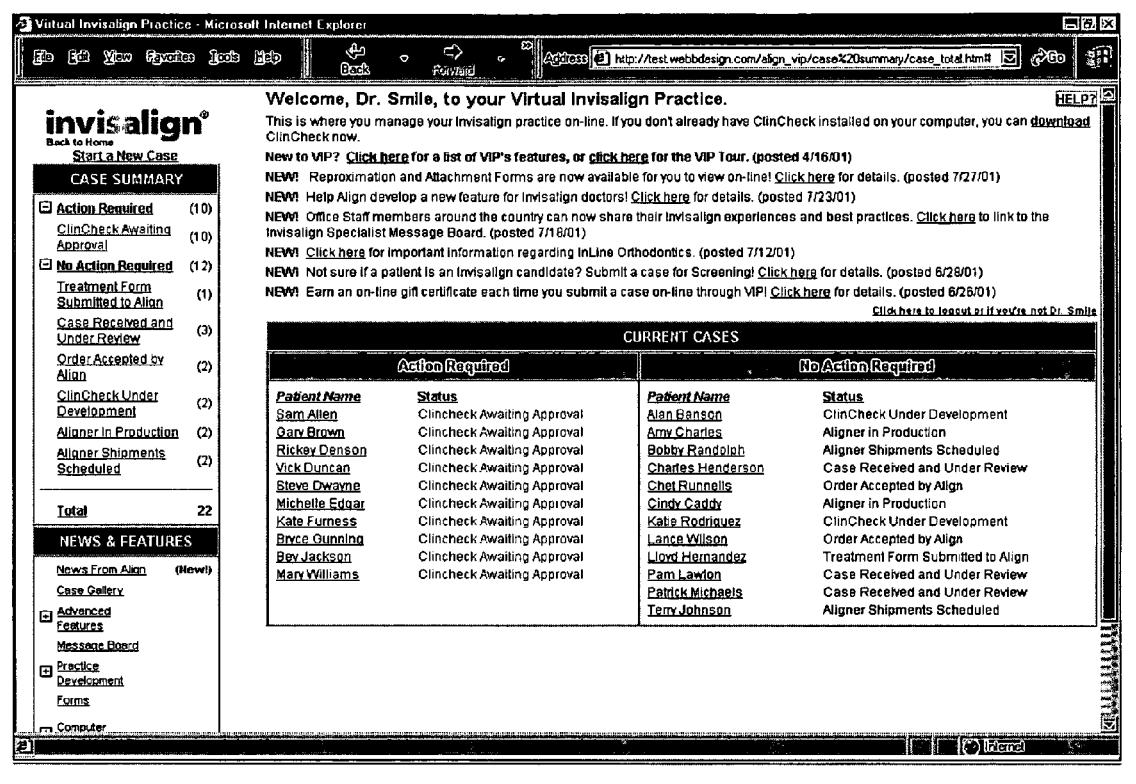

FIG. 11 shows an exemplary home page of the web-based interface. The web-based system of FIG. 11 allows users such as doctors to manage the system practices on-line. The user can view all aspects of the patients' cases on-line. The user can also order advertising and marketing materials, chat on-line with other system doctors, review the system's how-to tutorials, and link the user's personal website.

The web-based system helps users such as the treating doctors to ensure that appliances received from the provider will treat the patient the way the user intended. The system does this with a dynamic 3-D animation called a virtual treatment model. The system not only shows the user's patient's teeth going through their projected movement as a result of wearing the system appliances (aligners), but it also gives the user the ability to manipulate the model in time and space to insure the treatment sequence is exactly what the user had in mind. The system gives the user control over the aligners the user will receive: if the animation the user sees does not depict the treatment or outcome the user intended, the system allows the user to send feedback to the provider with instructions on how to re-set the case. After the provider has received the user's explicit approval, the appliances are manufactured and sent to the user's office.

When the user views the case online through the provider's web site (for example at www.invisalign.com), the system contacts the provider's computer systems over the Internet and downloads the treatment model to the user's computer at work or at home. The system then allows the user to play animation showing the treatment progressing over time, starting and stopping at any point during the treatment. It also allows the user to inspect the treatment from any angle, or from as far away or as close as the user likes.

The system allows the user to view the status of all the cases at any point in time. Within the home page, a Patient Chart appears on right hand side of the page. The chart is divided into two columns—those cases that require action—Action Required—and those that do not—No Action Required. Within these lists, a status will appear next to each patient's name. This status identifies the current point of treatment for the patient. For example, if the user has patient John Doe in the Action Required column, and his status reads Awaiting Your Approval, the user will need to view and approve of Mr. Doe's file in order to continue with his treatment.

Status categories that appear under Action Required can include the following:
  Awaiting Approval
  Treatment Form Waiting to be Submitted
  Case Refinement Waiting to be Submitted
  Screening Form Waiting to be Submitted
  Case Screening Result is Ready
  Case on Hold Awaiting New Impressions
  Case Waiting to be Resumed by Doctor
  Midcourse Correction Waiting to be Submitted
  Further Materials Required Statuses that can appear under No Action Required include the following:
  Treatment Form Submitted to the provider
  Case Received and Under Review
  Order Accepted by the provider
  Under Development
  Shipments Scheduled
  Aligners Shipped
  Case Refinement Submitted
  Case Currently Being Screened
  Case Hold Requested by Doctor
  Case Resume Requested by Doctor
  Cancellation Requested by Doctor
  Midcourse Correction Submitted Treatment Form Waiting to be Submitted. This means that the user started a standard Online Treatment Planning Form for a patient, but did not submit it to the provider. The case will be stored in VIP under this category until submiting it.

Case Received and Under Review. Case Received and Under Review is a category of patients whose clinical items (Treatment Planning Forms, PVS impressions, Bite Registrations, X-rays, Photos) the provider has received and in the process of confirming that these patients are candidates for the system treatment. If the case is accepted for treatment, the status will change to Order Accepted by the provider. If the case is not accepted for treatment, the status will change to Order Not Accepted by the provider and a representative will call the user's office.

Order Accepted. Order Accepted is a category of patients whose cases have been accepted for treatment by the provider. The next status the user will see for this patient will be Under Development. When this patient's file has been developed, the status will then become Awaiting Approval. At that time, feedback to the system will be required in order to continue processing the case.

Under Development. Under Development is a category of patients whose files are currently being developed by the provider. When the system is ready, the patient's status will change to Awaiting Approval. At that time, feedback to the system will be required in order to continue processing the case.

Awaiting Approval. Awaiting Approval is a category of patients' whose files are ready for review and feedback. To review a patient's file, the user can click on their name in the home page. The user will be linked to the patient's Summary Page where the user can view models. If the user accepts a patient's case, the status for the patient will change to The aligner in Production. If the user requests modification of the file, the status will change back to Under Development.

Shipments Scheduled. Shipments Scheduled is a category of patients' whose the aligners are currently being produced and are due to ship in the near term. To view a patient's scheduled ship date, the user can click on his or her name. The user will be linked to the patient's Summary Page where the user can view the ship date. Once the patient's the aligners are shipped, the status will change to Aligners Shipped.

Aligners Shipped. Aligners Shipped is a category of patients' whose the aligners have already shipped. The user can check the date the the aligners were shipped by clicking on the patient's name. The user will be linked to the patient's Summary Page where the user can view the ship date. This is the last status for a patient.

Case Refinement Waiting to be Submitted. Case Refinement Waiting to be Submitted is a category of patients' whose Case Refinement Form the user started, but did not yet submit to the provider. To submit this form for a patient, the user can click on the patient's name. The user will be linked to the patient's Summary Page. From this page the user can continue filling out the form and submit it to the provider. Once the form is submitted, the status will change to Case Refinement Submitted.

Case Refinement Submitted. Case Refinement Submitted is a category of patients' whose Case Refinement Form the user submitted to the provider. Once the provider begins developing a new file for these patients, the patient status will change to Under Development. When the system is ready, the patient's status will change to Awaiting Approval. At that time, feedback to the system will be required in order to continue processing the case.

Screening Form Waiting to be Submitted. Screening Form Waiting to be Submitted is a category of patients' whose Screening Forms the user started, but did not submit to the provider. To submit this form for a patient, a user can click on the patient's name. The user will be linked to the patient's Summary Page. From this page the user can continue filling out the form and submit it to the provider. Once the form is submitted, the status will change to Case Currently Being Screened.

Case Currently Being Screened. Case Currently Being Screened is a category of patients' whose Screening Forms the user submitted to the provider. These cases are currently being reviewed by the provider when the review process is complete, the patient status will change to Case Screening Result is Ready.

Case Screening Result is Ready. Case Screening Result is Ready is a category of patients' whose Screening Forms the user submitted to the provider and whose results are ready for review. These cases are currently being reviewed by the provider—when the review process is complete, the patient status will change to Case Screening Result is Ready. To review the case screening results for a patient, the user can click on the patient's name.

Case on Hold Awaiting New Impressions. Case on Hold Awaiting New Impressions is a category of patients' whose cases have been placed on hold by the provider due to unusable PVS impressions. When the provider places a case on hold, the user's office will be called so that steps can be taken to resume the case as quickly as possible.

Case Waiting to be Resumed by Doctor. Case Waiting to be Resumed by Doctor is a category of patients' whose cases the user has placed on hold—these cases will remain on hold until the user resumes them. To resume a case, the user can click on the patient's name in VIP. The user will be linked to the patient's Summary Page. From this page the user can click on the Resume this Case link.

Case Hold Requested by Doctor. Case Hold Requested by Doctor is a category of patients' whose cases the user has requested that The provider hold. Before The provider places the case on hold, the user will be called to confirm that the user wants The provider to stop processing the case. Once the provider has confirmed that the user wants the case placed on hold, the status will change to Case Waiting to be Resumed by Doctor. The user can then resume it by clicking on the patient's name in VIP. The user will be linked to the patient's Summary Page. From this page the user can click on the Resume this Case link.

Case Resume Requested by Doctor. Case Hold Requested by Doctor is a category of patients' whose cases the user has requested that the provider hold. Before the provider places the case on hold, the user's office will be called to confirm that the user wants the provider to stop processing the case. Once the provider has confirmed that the user wants the case placed on hold, the status will change to Case Waiting to be Resumed by Doctor. The user can then resume it by clicking on the patient's name. The user will be linked to the patient's Summary Page. From this page the user can click on the Resume this Case link.

Cancellation Requested by Doctor. Cancellation Requested by Doctor is a category of patients' whose cases the user has requested that the provider cancel. Before the provider cancels a case, the user's office will be called to confirm that the user wants the provider to stop processing the case. Once the provider has confirmed that the user wants the case placed on hold, the case will be removed from the database.

Midcourse Correction Waiting to be Submitted. Midcourse Correction Form Waiting to be Submitted is a category of patients' whose Midcourse Correction Forms the user started, but did not submit to the provider. To submit this form for a patient, the user can click on the patient's name. The user will be linked to the patient's Summary Page. From this page the user can continue filling out the form and submit it to the provider. Once the form is submitted, the status will change to Midcourse Correction Submitted. Once the provider has had a chance to review the user's request, the patient status will change to Under Development.

Midcourse Correction Submitted. Midcourse Correction Submitted is a category of patients' whose Midcourse Correction Forms the user recently submitted to the provider. Once the provider has had a chance to review the request, the patient status will change to Under Development.

Further Materials Required. Further Materials Required is a category of patients' whose files are incomplete and cannot be processed further until additional materials are sent to the provider. In most cases, this means that the Submission Box sent to the provider did not include all necessary patient materials. When a case enters this status, the provider will call the user's office to let the user know that further materials are required.

To view only certain cases, the user must click on the status category in the Case Summary box that the user is interested in viewing. For example, if the user would like to view only cases that are in the Awaiting Approval phase, the user clicks on that link. The patient chart on the right side of the page will now only display cases in the Awaiting Approval phase.

To return to a view of all the cases, the user clicks on Total to take the user back to the original patient chart. The user can also sort cases within any patient list by clicking on one of the column headings. For example, to sort cases by patient name, the user must click on the Patient Name heading. The cases will now be sorted in alphabetical order by patient name. The user can always identify how the patient list is sorted by noting which column heading is italicized.

Each of the patients in treatment has their own Patient Summary Page. The Patient Summary Page allows the user to view all aspects of a patient's case, from their file to their treatment history. To access a Patient's Summary Page, the user clicks on the name of the patient whose file the user would like to view. The user can find a list of all the patients on the Home Page. From the Patient Summary Page, the user can do each of the following:

View a Patient's Model
 View Static Images
 View Treatment History
 View On-line Forms—Attachment and Reproximation
 Create an Aligner Schedule
 Place a Case on Hold
 Cancel a Case One function supported by the system is to enable the user to complete an On-line Treatment Planning Form as quickly and as efficiently as possible.

On the Treatment Forms page the user can access the following:

On-line Treatment Planning Form
 Paper Treatment Planning Form
 Case Refinement Form
 Mid-course Correction Form A template called Treatment Preferences shown in FIG. 12 is used and allows the user to enter treatment information one time—this information is then incorporated into each form the user fills out, eliminating the need to enter redundant information each time the user submits a new case. The Treatment Preferences form will automatically appear in a separate window when the user clicks on the Start a New Case link for the first time. For each On-line Treatment Planning Form the user fills out, at the beginning of the form the user will be given the option of activating the Treatment Preferences for that form. The user can change the Treatment Preferences at any time by clicking on the Treatment Preferences link that appears after the user has clicked on the Start a New Case link.

In this system, the form does not allow the user to advance to subsequent pages until the current page is completely filled out. In addition, the form has built-in logic; it does not permit the user to send in a form that has contradicting inputs, nor can the user submit a case that does not meet predetermined case selection criteria. These features greatly increase the likelihood that each submitted case would be accepted for treatment. If the user needs help filling out the form, the user clicks on the question mark symbol within the form to view the comprehensive Help section.

Yet another feature is a Case Selection Expansion option. Case Selection Expansion allows experienced system doctors to submit cases beyond the limits of what is normally accepted through the On-line Treatment Planning Form. If the user is an experienced user who has submitted a large number of cases, the user is eligible for Case Selection Expansion. Once classified as an experienced user, the user will see a screen asking whether the user would like to use the standard On-line Treatment Planning Form or the Case Selection Expansion Form, which allows more flexibility. If the user selects the Case Selection Expansion Form, the user is prompted to sign a waiver. Besides relaxed case selection criteria for the Case Selection Expansion Form, the user will find the two submission forms are identical.

Yet another feature in this embodiment is case screening. If the user is not sure whether a case is appropriate for system treatment and would like feedback from the system, the user can use the Case Screening feature. The user must be able to submit digital photos on-line to use this feature. In one embodiment, to screen a new case, the user clicks on a Case Screening link, enters the office information and the patient's information, enters the treatment plan and goals for the patient, and uploads digital photos of the case—either individual photos or a composite photo. After submission, a professional reviewer at the provider reviews and provides comments and/or suggestions for treatment. If a patient's screening result is ready, that patient's status is listed as Case Screening Result is Ready. The user can then click on the patient's name to view the screening result and to submit the case for treatment.

The system can also handle case refinement situations. Case refinement occurs when additional the aligners beyond the last stage are needed to move a patient's teeth closer to the desired final outcome approved by the user in the system. If the user has a case that qualifies for Case Refinement, the user's next step is to submit a Case Refinement Form for that case. Once the user has submitted a Case Refinement Form, the user can track the status of the form through the VIP Home Page. When the form is submitted, the patient's status will change to Case Refinement Submitted. When a new file begins production, the status will change to Under Development. Once the file is ready for review, the status will change again to Awaiting Approval.

In instances when clinical results deviate from the original treatment plan such that the aligner(s) no longer fit, a Mid-Course Correction is necessary. This may be due to any of the following:

Patient underwent dental work during the course of treatment
 Poor patient compliance
 Treatment goal has changed
 Case has deviated from the approved course of treatment If the user has a case that qualifies for Mid-Course Correction, the next step is to submit a Mid-Course Correction Form for that case. Once the user has submitted a Mid-Course Correction Form, the user can track the status of the form through the Home Page. When the form is submitted, the patient's status will change to Mid-Course Correction Form Submitted. When a new file begins production, the status will change to Under Development. Unlike Case Refinement Cases, Mid-Course Correction files do not require feedback. Once the file is ready, the status will change again to Aligner Shipments Scheduled.

Figure 13A:
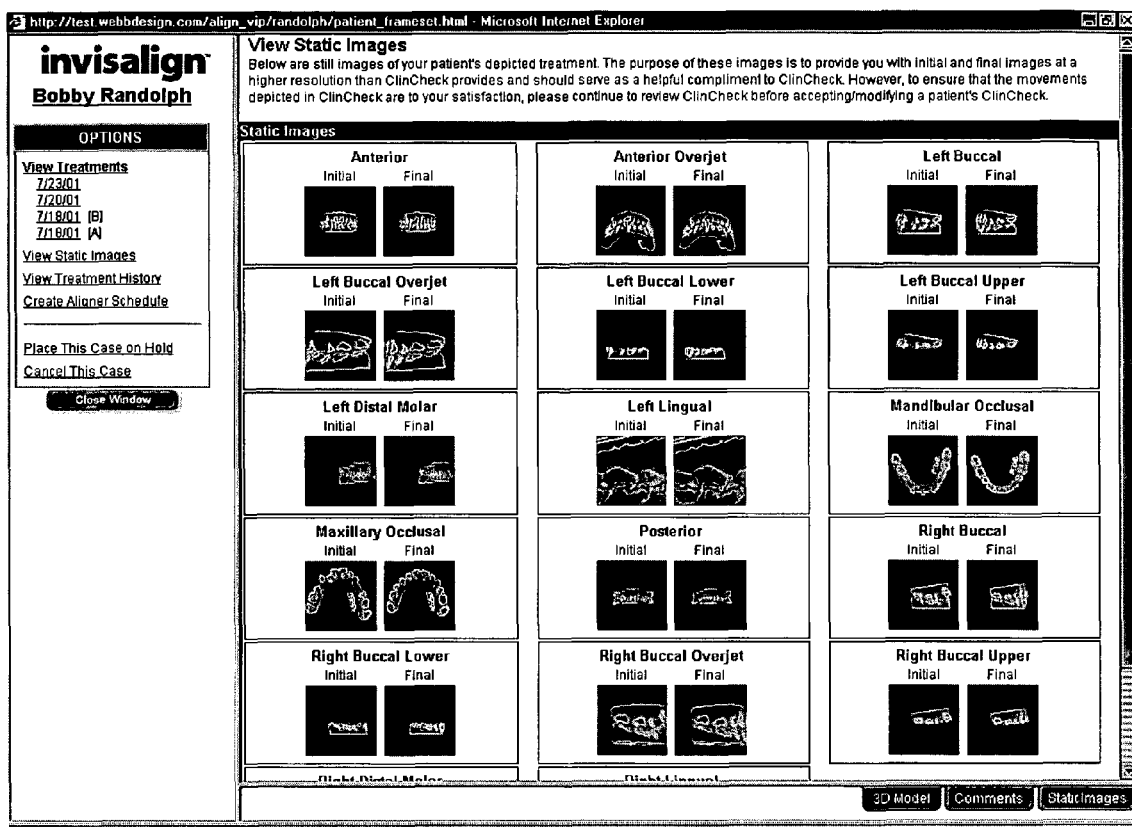
FIGS. 13A and 13B are exemplary drawings of a patient's teeth depicting initial and final high resolution images.
Figure 13B:
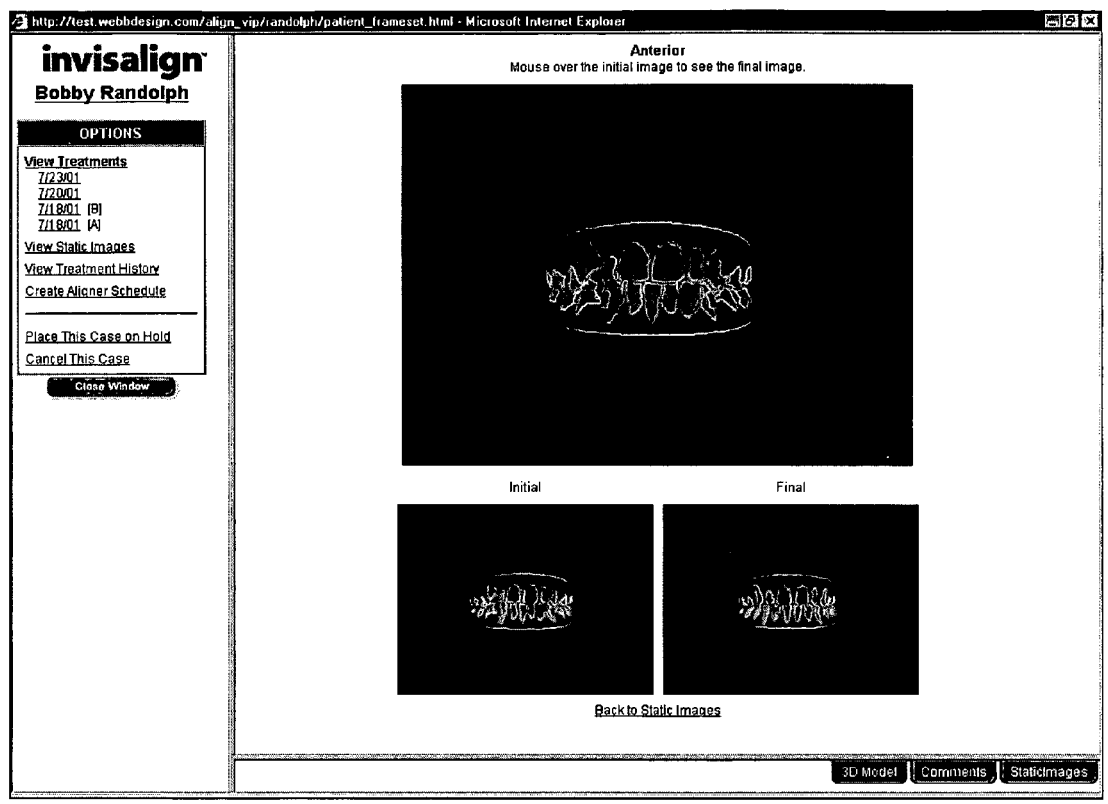

FIGS. 13A and 13B show exemplary views of Static Images of a patient's teeth. The benefit of the Static Images is that they provide the user with initial and final images of the depicted treatment at a high resolution. To view a patient's Static Images, the user can click on the View Static Images link within the Options left menu bar on the left side of a Patient's Summary Page. Alternatively, the user can access Static Images by clicking on the Static Images link at the bottom a Patient's Summary Page. Once viewing the images, the user can enlarge them for a better view by clicking on them.

FIG. 13B shows a Scroll Over Model—the user can scroll the mouse over the image to view the initial and final views of the patient's depicted treatment. The bottom images provide a side-by-side comparison of the initial and final views.

The system can also allow the user to view a patient's dental model. To view a patient's file, the user must click on the name of the patient whose file the user would like to view. The user can use the system to see many different views of a treatment model. The user can zoom in and out, hide the upper and lower arches, and rotate the model to see it from different angles. The user can choose to see the model from fourteen different pre-set angles. The user can rotate a model to any angle, making it seem to spin in the window. The user can position the mouse inside the model window and click and hold the left mouse button while dragging the mouse in the direction that the user wants to move the model. The model rotates as the user moves the mouse. As an example, the user can start with the right buccal view of the model. The user must click and hold the left mouse button and drag the mouse from right to left. As the user does so, the model rotates so the user can see all of the teeth as the model moves.

If the user would like to take a closer look at a model, the user can zoom in. Conversely, if the user would like to see a view of the model from further away, the user can zoom out. To zoom, the user must press and hold the Control (Ctrl) key. Positioning the mouse inside the model window, the user must click and hold the left mouse button and drag the mouse up to zoom out and down to zoom in. The further the user drags, the further the user will zoom. Alternatively, if the mouse has a mouse wheel, the user can turn the mouse wheel to zoom in and out. The user can also slide the model up and down, and left and right. To slide the model, the user must press and hold the Shift key, then click and drag the mouse. The model moves in the direction of the mouse motion. This motion can be useful when the user has a zoomed in view of the model, and the user would like to see another part of the model. The user can hide the upper or lower arch to see an unobstructed view of the other arch. This is useful, for example, when looking at the occlusal surface of either arch. To hide the upper arch, the user must click the checked box next to Show Upper Jaw in the left menu bar. The check mark is removed and the upper arch disappears from view. To hide the lower arch, the user must click the checked box next to Show Lower Jaw in the Dialog box. The check mark is removed and the lower arch disappears from view. When the user hides either arch, the user can still rotate the model so the user can see it from any angle. Once the user has hidden an arch, the user can show it again. To show an arch once the user has hidden it, the user must re-select the Show Upper Jaw or Show Lower Jaw command from the left bar menu. When the boxes show check marks, the arches are shown. The user can also select the level of detail of the model. On the left menu bar, the options Show Low Resolution and Show High Resolution appear. By default, Show Low Resolution is selected. Alternatively, the user can select Show High Resolution to show a more detailed version of the model.

To print a model in its current view, the user must click the Print icon or right-click the mouse over the window and select Print from the Right Mouse Button menu.

The animation allows the user to see how a patient is projected to progress using the system. Using the animation controls located in the lower right corner of the model window, the user can play, stop, rewind and fast-forward the animation. The user can also step forward or backward through the animation stage by stage (a stage corresponds to one set of aligners). To play an animation, the user must click the Play button. The Play button then becomes the Stop button. To stop an animation, the user must click the Stop button. To resume playing the animation, the Play button is clicked. When the user rewinds an animation, the model returns to its beginning position. To rewind an animation, the user can click the Rewind (<<) button. To rewind the model stage-by-stage, the user can click the Back (<) button and the model will rewind one stage. When the user fast-forwards an animation, the model advances to its final position. To fast-forward an animation, the user can click the Fast Forward (>>) button. To view the model stage-by-stage, the user can click the Forward (>) button and the model will advance one stage.

Other features supported by the web-based system of the present invention includes Viewing Current/Archived News; Viewing the Case Gallery where the user can view before and after pictures of past system patients by visiting the system Case Gallery; Downloading All Files at Once, where the user can view the patients' cases without being connected to the Internet; Printing a List of All Patients; and a Message Board, where the users talk with other system doctors to share experiences with the product so the user can learn from and offer suggestions to other doctors who are using the provider.

The invention has been described in terms of particular embodiments. Other embodiments are within the scope of the following claims. For example, the three-dimensional scanning techniques described above may be used to analyze material characteristics, such as shrinkage and expansion, of the materials that form the tooth castings and the aligners. Also, the 3D tooth models and the graphical interface described above may be used to assist clinicians that treat patients with conventional braces or other conventional orthodontic appliances, in which case the constraints applied to tooth movement would be modified accordingly.

What is claimed is:

1. A virtual health-care electronic commerce community, comprising:
    a server that transmits via a network information relating to an orthodontic treatment of a patient, the network coupled to one or more treating professional computers, the server comprising storage media having one or more instructions that if executed cause the server to:
    access a database comprising a treatment plan for providing orthodontic treatment to the patient, the treatment plan comprising a plurality of digital models of the patient's teeth corresponding to successive tooth arrangements for moving teeth from a first arrangement toward a desired final arrangement;
    transmit a manipulable 3-D model, selected from the database, to a treating professional computer for generating one or more modifications to the manipulable 3-D model;
    receive data from the treating professional computer, the data comprising one or more modifications to the 3-D model; and
    transmit visualization data in response to a request from the treating professional, the visualization data comprising information for visually displaying an aspect of the patient's treatment according to the treatment plan.

2. The community of claim 1, wherein the visualization data comprises at least one of a right buccal view, a left buccal view, a posterior view, an anterior view, a mandibular occlusal view, a maxillary occlusal view, an overjet view, a left distal molar view, a left lingual view, a lingual incisor view, a right lingual view, a right distal molar view, an upper jaw view, and a lower jaw view.

3. The community of claim 1, wherein the visualization data comprises information for visually displaying an expected outcome of the orthodontic treatment.

4. The community of claim 1, wherein the visualization data comprises information for visually displaying the patient's teeth before and after treatment.

5. The community of claim 1, wherein the visualization data comprises one or more animations showing progress of the patient's treatment.

6. The community of claim 1, wherein the one or more modifications to the 3-D model comprises adjustment to a position of at least one tooth in the 3-D model.

7. The community of claim 1, wherein the plurality of 3-D models comprises models of the patient's teeth corresponding to an initial arrangement, one or more intermediate arrangements, and a desired final arrangement to be achieved by orthodontic treatment.

8. The community of claim 1, wherein the treating professional comprises a dentist or an orthodontist.

9. The community of claim 1, further comprising one or more partners coupled to the network.

10. The community of claim 1, wherein the server is accessible by a user of the treating professional computer using a browser.

11. A method for communicating information relating to an orthodontic treatment of a patient, comprising:

providing a server for transmitting via a network information relating to treatment of the patient, the network coupled to one or more treating professional computers;

accessing a database comprising a treatment plan for providing orthodontic treatment to the patient, the treatment plan comprising a plurality of digital models of the patient's teeth corresponding to successive tooth arrangements for moving teeth from a first arrangement toward a desired final arrangement;

transmitting a manipulable 3-D model, selected from the database, to a treating professional computer for generating one or more modifications to the manipulable 3-D model;

receiving data from the treating professional computer, the data comprising one or more modifications to the 3-D model; and transmitting visualization data in response to a request from the treating professional, the visualization data comprising information for visually displaying an aspect of the patient's treatment according to the treatment plan.

* * * * *